United States Patent [19]

Suorsa et al.

[11] Patent Number: 5,522,392
[45] Date of Patent: *Jun. 4, 1996

[54] ENHANCING INTRAVASCULAR ULTRASONIC BLOOD VESSEL IMAGE

[75] Inventors: Veijo Suorsa; Axel Brisken, both of Fremont, Calif.

[73] Assignee: Cardiovascular Imaging Systems, Inc., Sunnyvale, Calif.

[*] Notice: The term of this patent shll not extend beyond the expiration date of Pat. No. 5,363,849.

[21] Appl. No.: 340,180

[22] Filed: Nov. 15, 1994

Related U.S. Application Data

[63] Continuation of Ser. No. 188,173, Jan. 26, 1994, Pat. No. 5,363,849.

[51] Int. Cl.$^6$ ........................................................ A61B 8/00
[52] U.S. Cl. ............................... 128/661.08; 128/662.02
[58] Field of Search ......................... 128/661.08, 661.09, 128/661.10, 662.01; 73/629, 861.25; 364/413.25

[56] References Cited

U.S. PATENT DOCUMENTS

| | | | |
|---|---|---|---|
| 4,583,552 | 4/1986 | Iinuma | 128/661.09 |
| 4,751,847 | 6/1988 | Katakura et al. | 73/629 |
| 4,794,931 | 1/1989 | Yock . | |
| 4,967,753 | 11/1990 | Haase et al. . | |
| 5,000,185 | 3/1991 | Yock . | |
| 5,111,825 | 5/1992 | Nishiyama et al. | 128/661.09 |
| 5,174,295 | 12/1992 | Christian et al. . | |
| 5,243,988 | 9/1993 | Sieben et al. . | |

Primary Examiner—George Manuel
Attorney, Agent, or Firm—Townsend and Townsend and Crew; Kenneth R. Allen

[57] ABSTRACT

In an intraluminal ultrasound imaging system, ultrasound echoes representing vessel walls are distinguished from ultrasound echoes from blood by detecting and examining the phase of all received ultrasound echoes, extracting selected parameters from the phase information and utilizing the extracted parameters to suppress ultrasound echoes representing blood, thereby to enhance the lumen-to-vessel wall contrast. In a first embodiment, parameters are derived from a phase difference between echoes in approximately the same spatial location, including comparisons between neighboring image vectors of the same image frame or comparison between vectors on successive image frames. Selected parameters may be extracted based on statistics of the phase signal or the phase difference signal or from the slope of the phase difference or the phase signal, either between neighboring image vectors in the same image frame or between images of successive image frames. The extracted parameters are used as weights which are applied to the discrete image data to yield a final image. In a specific embodiment, weighted image information may modulate image information obtained by convention amplitude detection. As a final processing step, the mean signal amplitude in the region of blood flow is reduced as compared to an image detected using conventional amplitude detection means.

21 Claims, 14 Drawing Sheets

ENHANCING INTRAVASCULAR ULTRASONIC BLOOD VESSEL IMAGE

This is a continuation of application Ser. No. 08/188,173 filed Jan. 26, 1994, now U.S. Pat. No. 5,363,849

COPYRIGHT NOTICE

A portion of the disclosure of this patent document contains material to which a claim of copyright protection is made. The owner has no objection to the facsimile reproduction of the patent document or the patent disclosure, as it appears in the Patent and Trademark Office patent file or records, but reserves all other rights whatsoever.

BACKGROUND OF THE INVENTION

This invention relates to high resolution intravascular imaging and more particularly to intraluminal ultrasound imaging and techniques for enhancing image quality.

In intraluminal ultrasound imaging, the production of high resolution images of vessel wall structures requires imaging at high ultrasound frequencies. Vectors are created by directing focused ultrasonic pressure waves radially from a transducer in a catheter and collecting echoes at the same transducer from the target area. A plurality of radial vectors from the rotated transducer comprises an image frame. The backscatter from blood cells in such an image is a significant problem in high frequency intraluminal ultrasound imaging, since the scattering of ultrasound from blood cells is proportional to the fourth power of the frequency such that the higher the ultrasound frequency the more pronounced is the backscatter from blood. As a result, echoes from blood degrade the lumen-to-vessel wall contrast.

It is desirable to provide imaging over a broad range of frequencies, especially higher ultrasonic frequencies. Therefore, echoes in the ultrasound image due to backscatter from blood must either be removed or suppressed to a level at which wall structures can be distinguished from blood. Since blood is typically in motion relative to the image of interest, an individual frame will contain speckle due to the interference of blood constituents. One technique for enhancing image quality is to average successive image frames thereby to smooth out the impact of speckle (that is, the irregular pattern of backscatter from blood) in the intraluminal ultrasound images. However, such frame averaging is not effective in reducing the mean echo amplitude from the region of blood flow, and it cannot totally remove blood echoes from the image. What is needed is a mechanism for encoding or encrypting blood-induced echoes to allow a display of intraluminal ultrasound images free of blood-induced echoes.

Background information on the subject of intravascular ultrasonography is found in U.S. Pat. No. 4,794,931 and related U.S. Pat. No. 5,000,185.

SUMMARY OF THE INVENTION

According to the invention, in an intraluminal ultrasound imaging system, ultrasound echoes representing vessel walls are distinguished from ultrasound echoes from blood by detecting and examining the phase of all received ultrasound echoes, extracting selected parameters from the phase information and utilizing the extracted parameters to suppress ultrasound echoes representing blood, thereby to enhance the lumen-to-vessel wall contrast. In a first embodiment, parameters are derived from a phase difference between echoes in approximately the same spatial location, including comparisons between neighboring image vectors of the same image frame or comparison between vectors of successive image frames. Selected parameters may be extracted based on statistics of the phase difference signal or from the slope of the phase difference signal, either between neighboring image vectors in the same image frame or between vectors of successive image frames. The extracted parameters are used as weights which are applied to the discrete image data to yield a final image. In a specific embodiment, the image information obtained by conventional amplitude detection is weighted by parameters extracted from the phase information. As a result, the mean signal amplitude in the region of blood flow is reduced as compared to an image detected using conventional amplitude detection means only.

The invention will be better understood by reference to the following detailed description in connection with the accompanying drawings.

DESCRIPTION OF SPECIFIC EMBODIMENTS

The following is a functional description of apparatus which is used for processing image data according to the invention. The specific type of hardware is dependent upon the choice of technology employed to realize the signal processing functions herein described. Analog signal processing or specialized digital signal processing, including software-based digital signal processing, could be employed without departing from the spirit and scope of the invention.

Figure 1:
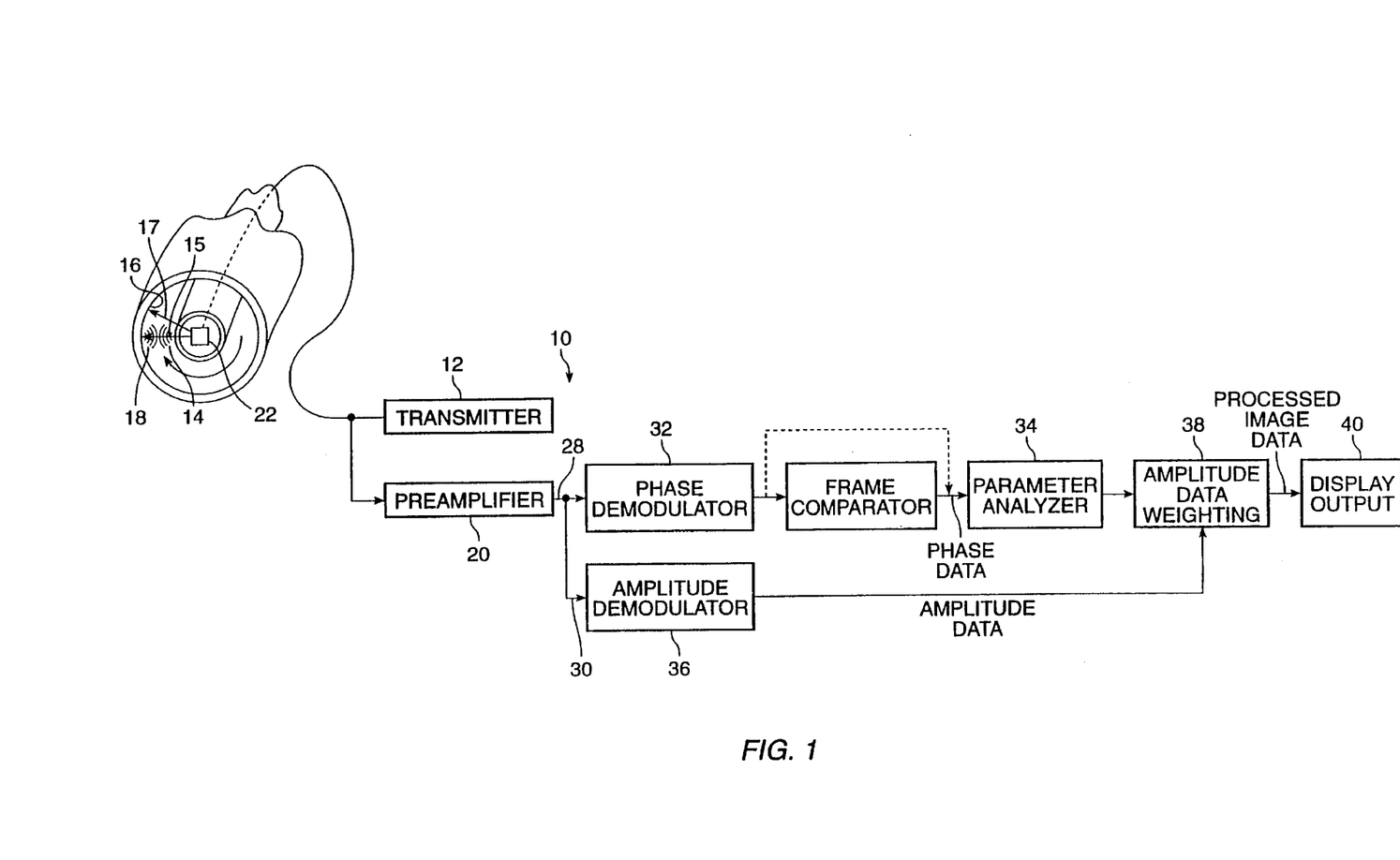
FIG. 1 is a block diagram of an intravascular ultrasonic imaging system in accordance with the invention.

Referring to FIG. 1, there is shown a block diagram of a type of intravascular ultrasonic imaging system 10 in accordance with the invention. An ultrasonic transmitter 12 generates ultrasonic signals 14 of for example 5 MHz to 50 MHz, which is directed to an intravascular target 16 to cause reflections in the form of ultrasonic echo signals 18 from the intravascular structures, including blood (not shown). A preamplifier 20 receives an electronic representation of the ultrasonic echo signals 18 from the transducer 22 as a one-dimensional time-domain signal. The electrical signal is split, to be directed on a phase path 28 and an amplitude path 30. In the phase path, the signal is phase demodulated by a phase demodulator 32, then the phase signal is applied to a frame comparator which compares phase of successive frames to obtain differential phase data, which is in turn passed to a parameter analyzer 34. (Alternatively, difference in phase data may be derived by comparing neighboring vectors of the same image frame.)

The amplitude path 30 applies the signal to an amplitude demodulator 36, such as an envelope detector, and the resultant amplitude data is applied to a weighting processor 38. The output of the parameter analyzer 34 is employed to weight the amplitude data from the amplitude demodulator 36, and the processed image data resulting from the weighting processing is provided to a display or other image output device 40. The undesired artifacts of the image data are suppressed as a result of the weighting process to inhibit the interference caused by moving blood in the intravascular region under examination.

Figure 2A:
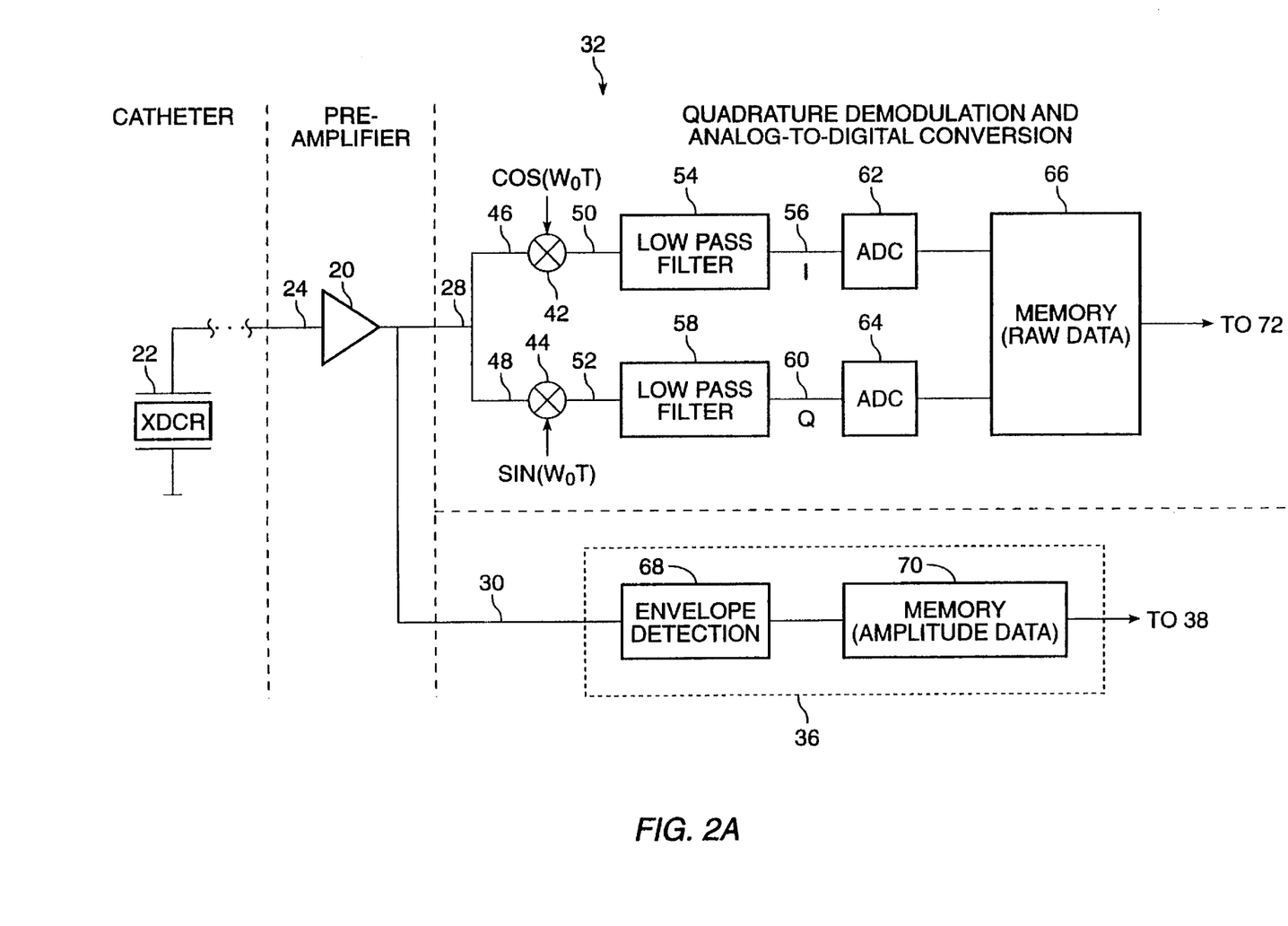
FIG. 2A is a schematic block diagram illustrating one form of front end processing in accordance with the invention.

FIG. 2A is a schematic block diagram illustrating data extraction processing in accordance with the invention. Preferably an analog representation of the electrical signal 24 is applied at the input of the preamplifier 20 for the phase demodulator 32. The front end of the phase demodulator 32 separates the analog input signal into an in-phase phase component and a quadrature-phase phase component by multiplying with respective multipliers 42, 44, the phase path signal, and specifically in-phase path 46 by $\cos \omega_0 t$ and quadrature-phase path 48 by $\sin \omega_0 t$, where $\omega_0 = 2\pi f_0$, $f_0$ is the reference frequency and t is time. The respective products on signal lines 50 and 52 are low-pass filtered by low-pass filter 54 to produce an analog in-phase phase component 56 (I) and by low-pass filter 58 to produce an analog quadrature-phase phase component 60 (Q). The I signal is then converted to digital form by first analog-to-digital converter (ADC) 62, and the Q signal is then converted to digital form by a second ADC 64. The digitized I and Q signals (the digitized in-phase component representation and the digitized quadrature-phase component representation) are then each stored as raw data in a digital memory 66 for "raw data" (data requiring further processing) prior to further processing in subsequent subsystems of the phase demodulator 32. On the amplitude path 30, the amplitude demodulator 36 includes an envelope detector 68 and memory means 70 for storing the resultant amplitude data produced by the envelope detector 68.

Figure 2B:
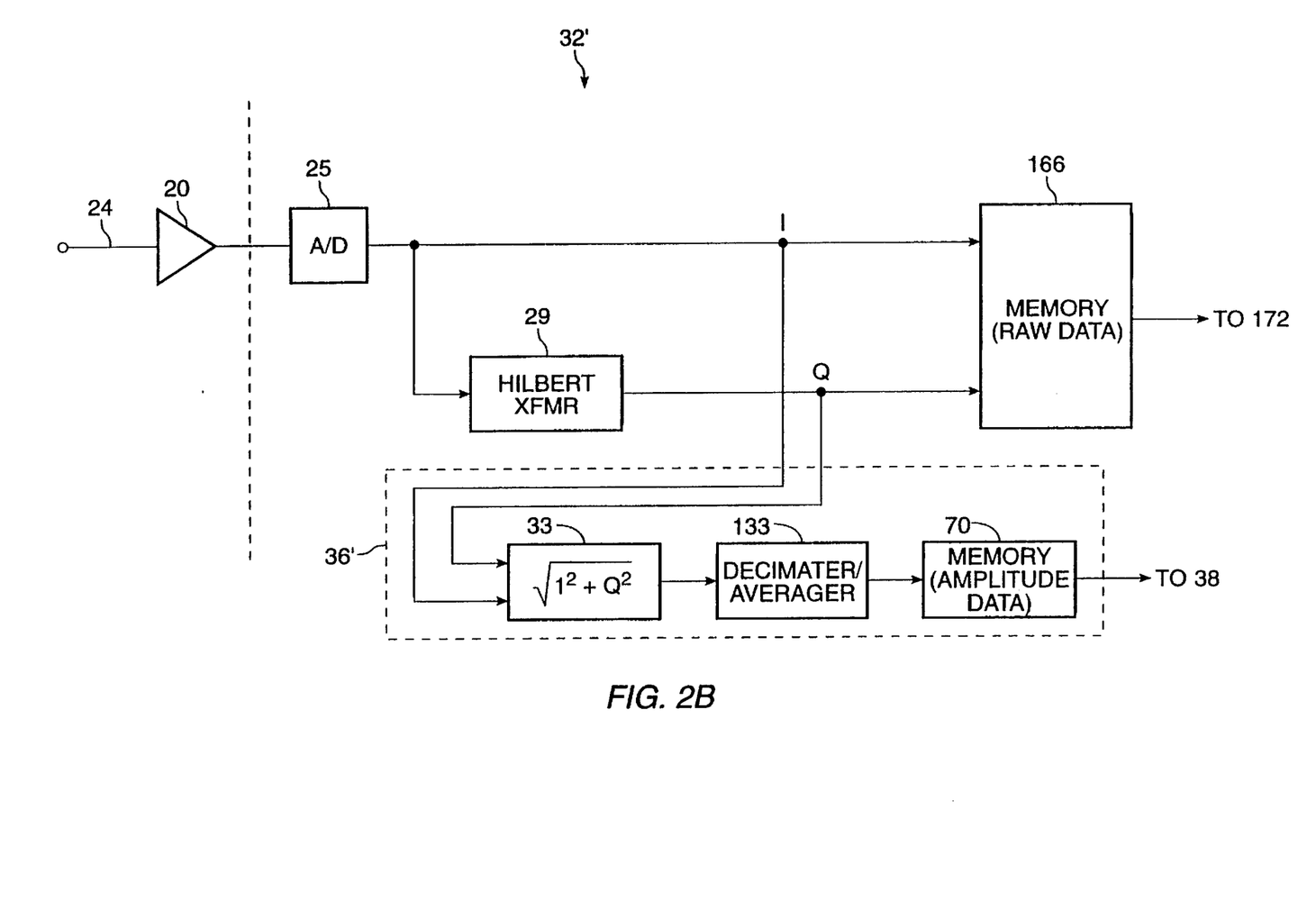
FIG. 2B is a schematic block diagram illustrating another form of front end processing in accordance with the invention.

Alternatively, referring to FIG. 2B, a single analog to digital converter 25 at the front end of the digital phase demodulator 32' converts the analog signal to digital form, and the resultant digital signal is processed in the digital time domain to extract directly the digitized in-phase component representation (the output of analog to digital converter 25) and the digitized quadrature-phase component representation (through a Hilbert transform processor 29), the outputs of which are stored in the raw data memory 166 for subsequent processing. Amplitude data is extracted by means of a digital detector means 36' with a digital envelope detector 33 which computes the square root of the sum of the squares of the I and Q components. In this implementation a decimator or averager 133 functions to reduce the data rate to that rate which output from analog envelope detection 68 (FIG. 2A) for data storage in memory 70.

Figure 3A:
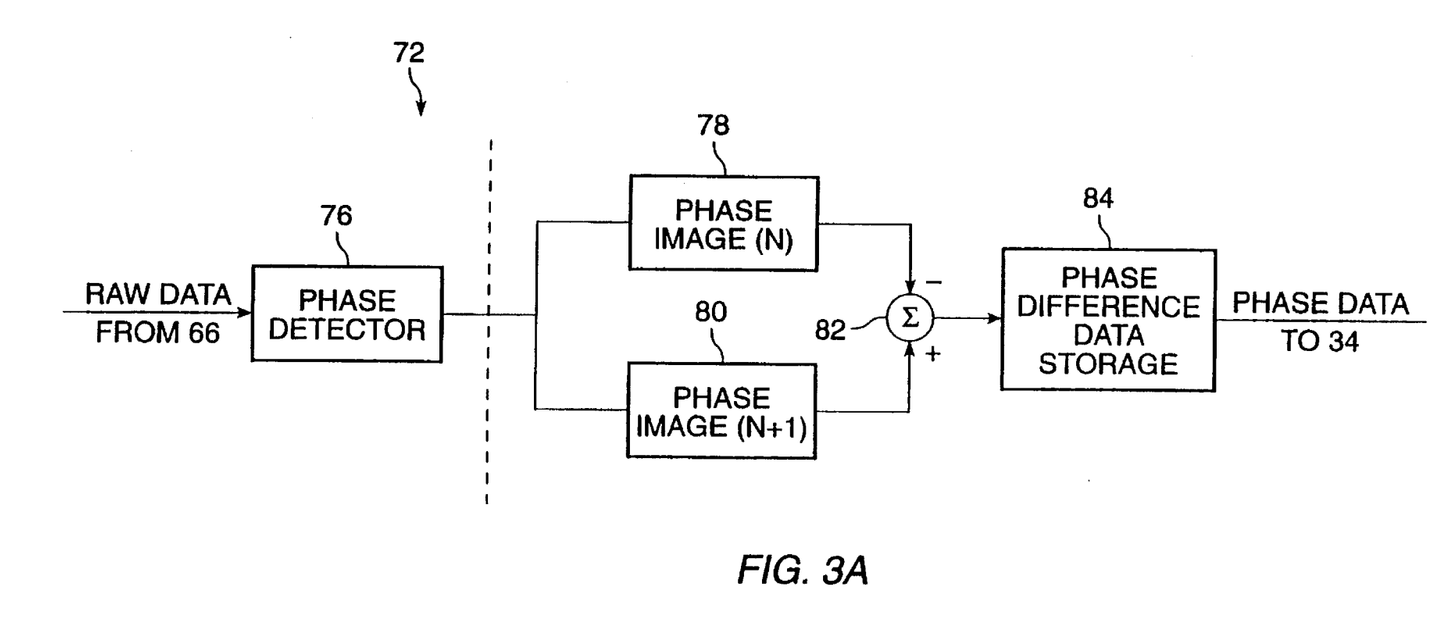
FIG. 3A is a block diagram of a multiple vector processor for generating a phase difference image in accordance with the invention.

Referring to FIG. 3A there is shown one type of processing subsystem 72 useful in the phase demodulator 32 illustrating how phase difference information may be derived. Raw data from raw data memory 66 is phase detected in a phase detector 76 as a phase angle by the simple relationship:

$$\phi = \arctan(Q/I)$$

for each frame of data. Thereafter the quotient $\phi$ at time N is passed to first phase image storage (N) 78, and the next quotient $\phi$ at time N+1 is passed to a second phase image storage (N+1) 80. The phase difference information is extracted by means of a summer 82 by subtracting the phase angles of two successive images to obtain phase difference data which are stored in a phase difference data memory 84. A cumulative phase difference is thereupon accumulated for use in subsequent processing. Alternatively, phase difference information is determined by means of summer 82 by subtracting the phase angles of two neighboring vectors in the same image to obtain phase difference data.

Figure 3B:
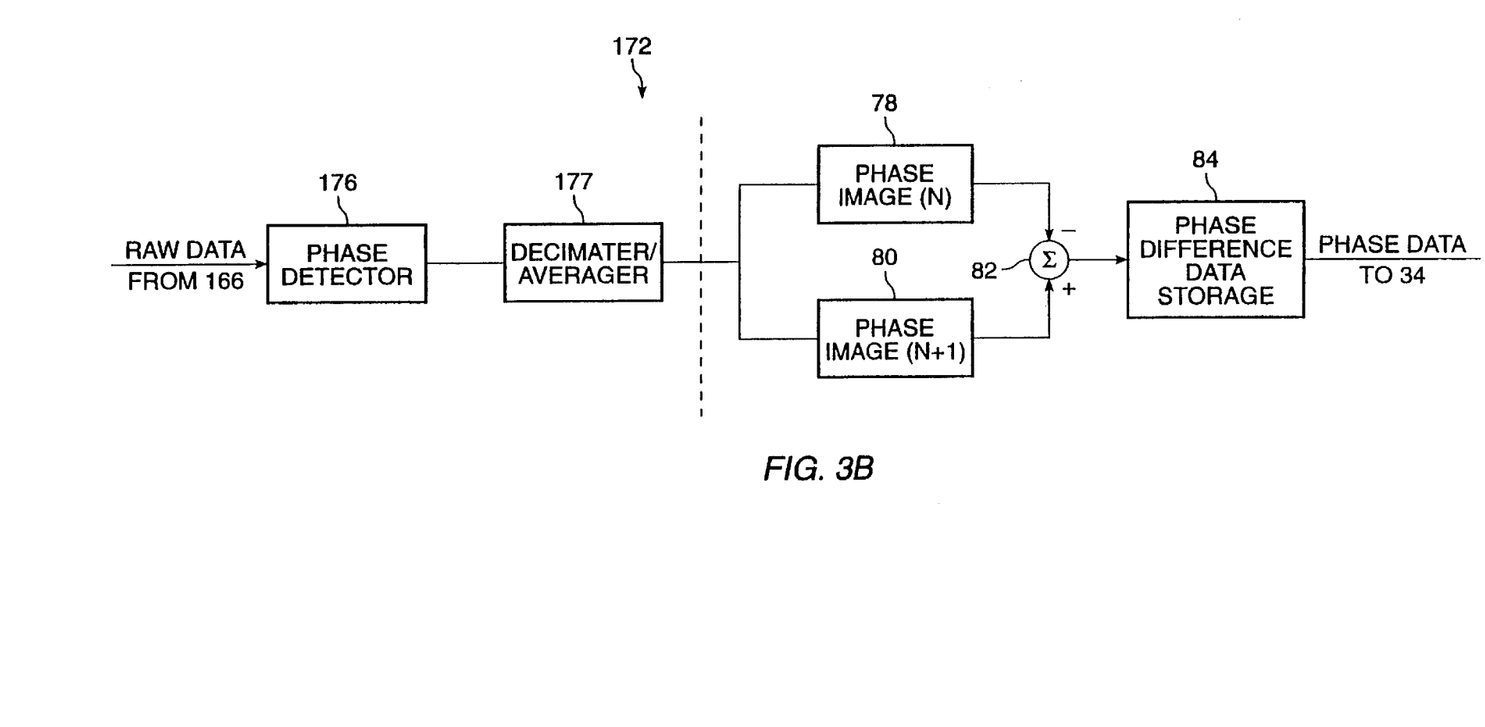
FIG. 3B is a block diagram of a multiple vector processor for generating a phase difference image according to another form of front-end processing in accordance with the invention.

Alternatively, referring to FIG. 3B, there is shown an alternate type of processing subsystem 172 (corresponding to pre-processing of FIG. 2B) useful in the phase demodulator 32 illustrating how phase difference information may be derived. Raw data from raw data memory 166 is phase detected in a phase detector 176 as the phase angle by the simple relationship:

$$\phi = \arctan(Q \text{ representation}/I \text{ representation})$$

for each from of data. Data rates are reduced to those of the analog path (FIGS. 2A, 3A) by the decimator/averager functional element 177. Subsequent processing is identical to that described above depicted in FIG. 3A.

Figure 4:
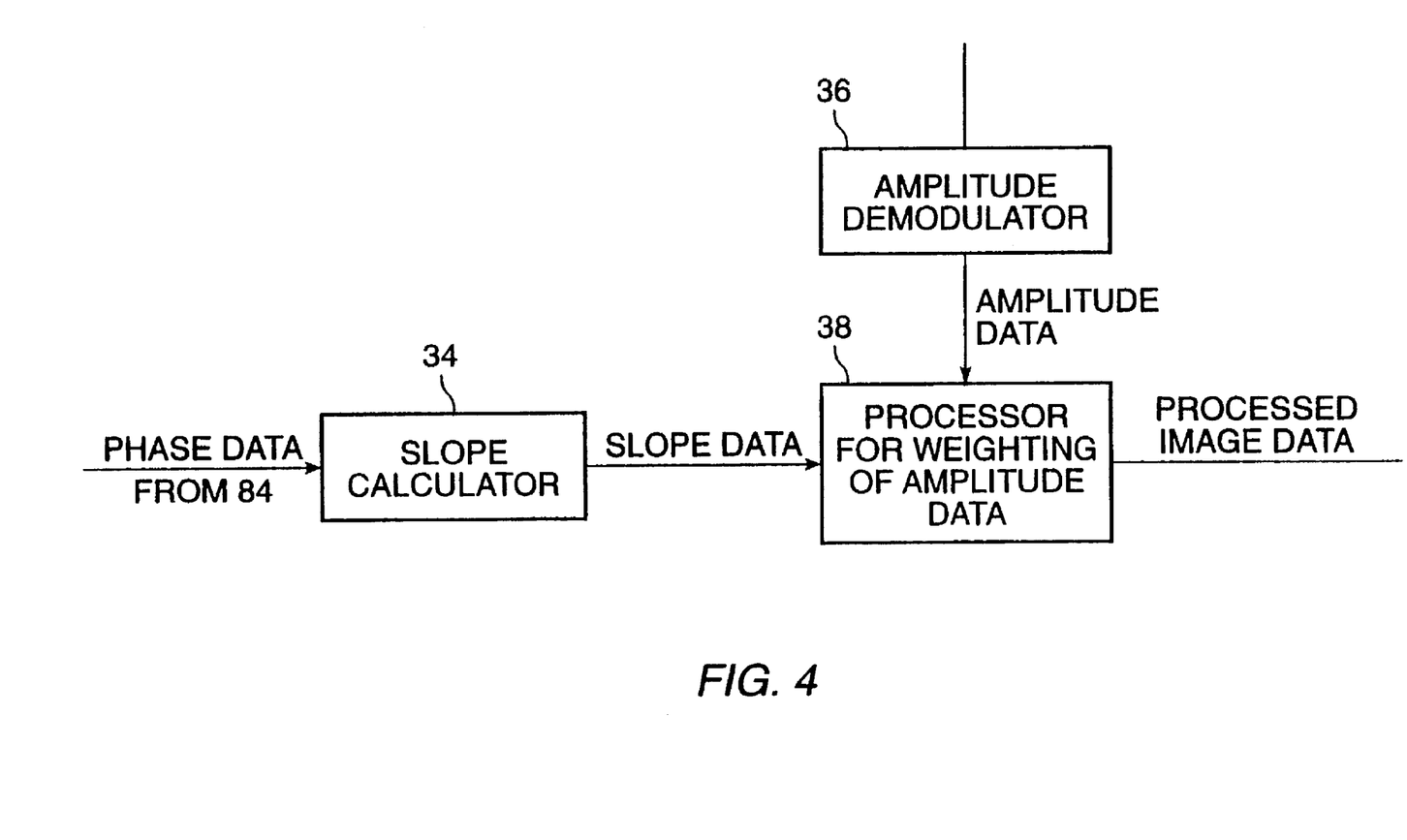
FIG. 4 is a block diagram of a first alternative embodiment for producing processed image data according to the invention.

The signal representing the slope of the phase difference is used to manipulate the signal obtained from the envelope detector 36 (FIG. 2A) or 36' (FIG. 2B). Referring to FIG. 4, phase data from the phase difference data memory 84 (FIG. 3A or 3B) is applied to a slope calculator, or more generically a parameter analyzer 34, which in this embodiment extracts the slope of the phase difference signal and supplies it as slope data to weighting processor 38, which in turn weights the amplitude data from amplitude demodulator 36 and processes the data as hereinafter explained to produce processed image data.

To obtain the slope data, the slope calculator (parameter analyzer) 34 is operative to calculate the moving average of the phase differences. The moving average comprises approximately 2 to 20 wavelengths of ultrasound signal data. In the weighting processor 38, a processed envelope $ENV_W$ is computed according to the relationship:

$$ENV_W = ENV_0(1 - SQRT(|NSLOPE|))$$

where $ENV_W$ is the processed envelope or image data, $ENV_0$ is the conventionally detected amplitude data from the amplitude demodulator 36, and $|NSLOPE|$ is the absolute value of the normalized slope of the phase difference, NSLOPE being the slope data from the slope calculator 34.

Figure 5:
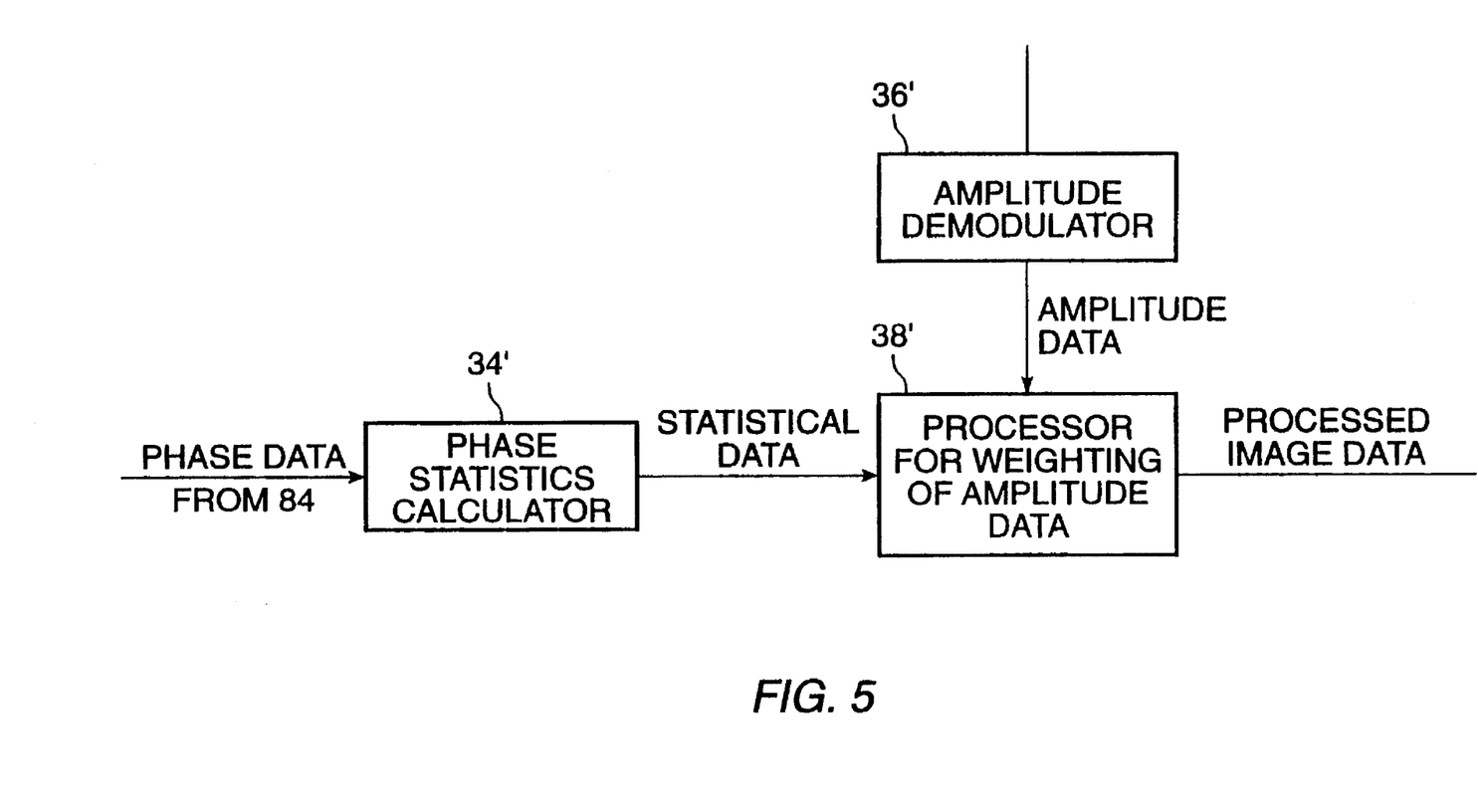
FIG. 5 is a block diagram of a second alternative embodiment for producing processed image data according to the invention.

In FIG. 5, an alternate technique for obtaining weighting parameters is illustrated which is a phase statistics calculator or parameter analyzer 34'. The standard deviation of the phase difference is calculated from an extended data segment (corresponding to two to about twenty wavelengths of the ultrasound signal). Similarly, the mean of the phase difference may also be extracted. The statistical data on standard deviation so obtained is applied to weighting processor 34' where it is used for weighting the amplitude detected data from amplitude demodulator 36 or 36' according to the following relation:

$$ENV_w = SF * ENV_0 / STD_0$$

where $ENV_w$ is the processed envelope or image data, $ENV_0$ is the conventionally detected amplitude data from the amplitude demodulator 36 or 36', $STD_0$ is the standard deviation of the phase difference within the data window, and SF is a scale factor. The scale factor SF is merely for scaling the output and is defined as:

$$SF = Max[ENV_w] / Max[ENV_0 / STD_0]$$

where Max represents the largest value of the data set in parentheses.

The weighted envelope data is plotted or displayed to show an image with reduced speckle from blood.

Referring to FIG. 6 through FIG. 13, there are shown various waveforms which illustrate how information from a sample data set is processed to obtain the desired signal.

Figure 6:
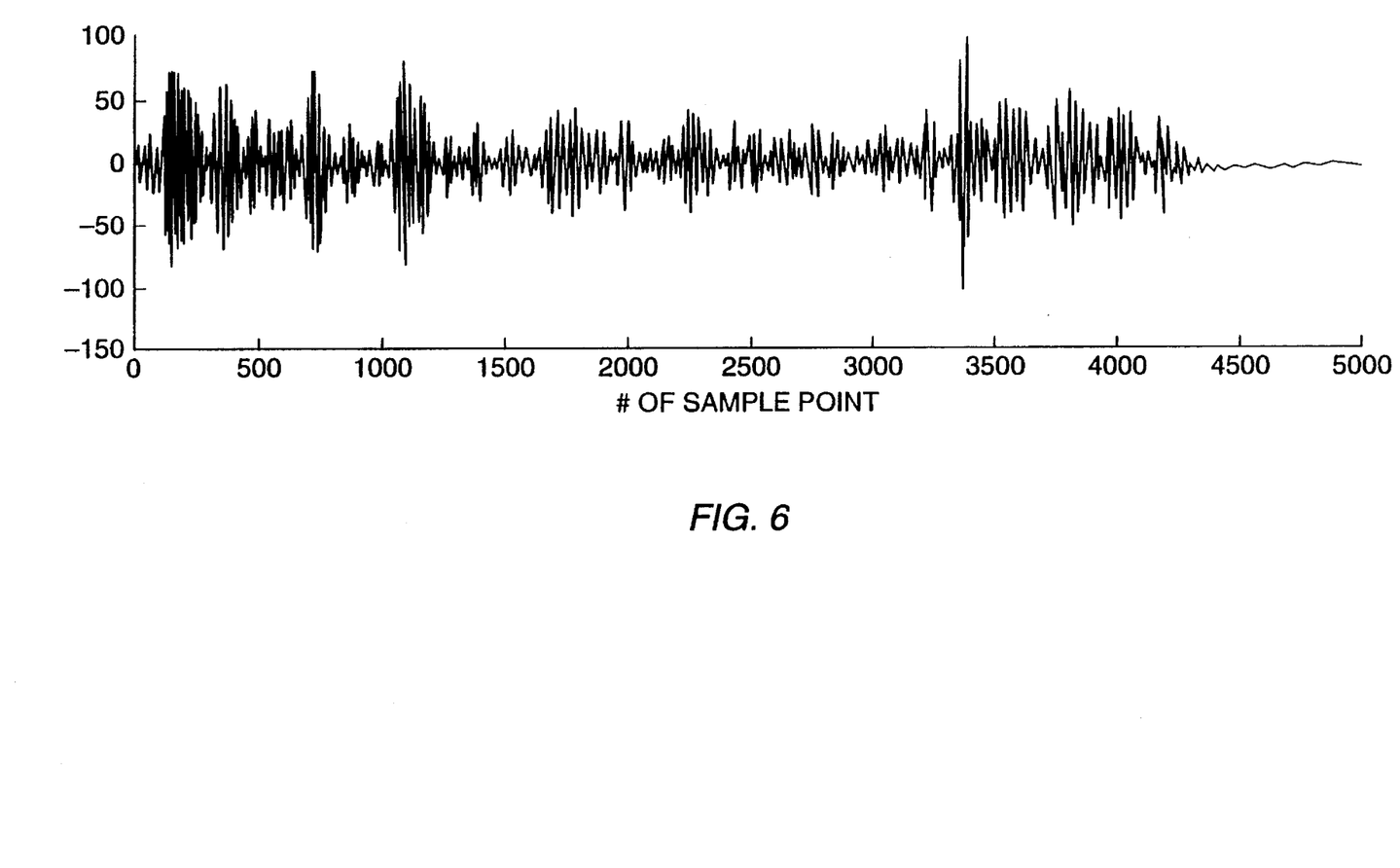
FIG. 6 is an illustrative waveform diagram at the output of the radio frequency preamplifier of the apparatus according to the invention.

FIG. 6 is an illustrative waveform at the output of the preamplifier 20 at the input of the front end of the phase demodulator 32 (FIG. 2A) or 32' (FIG. 2B).

Figure 7:
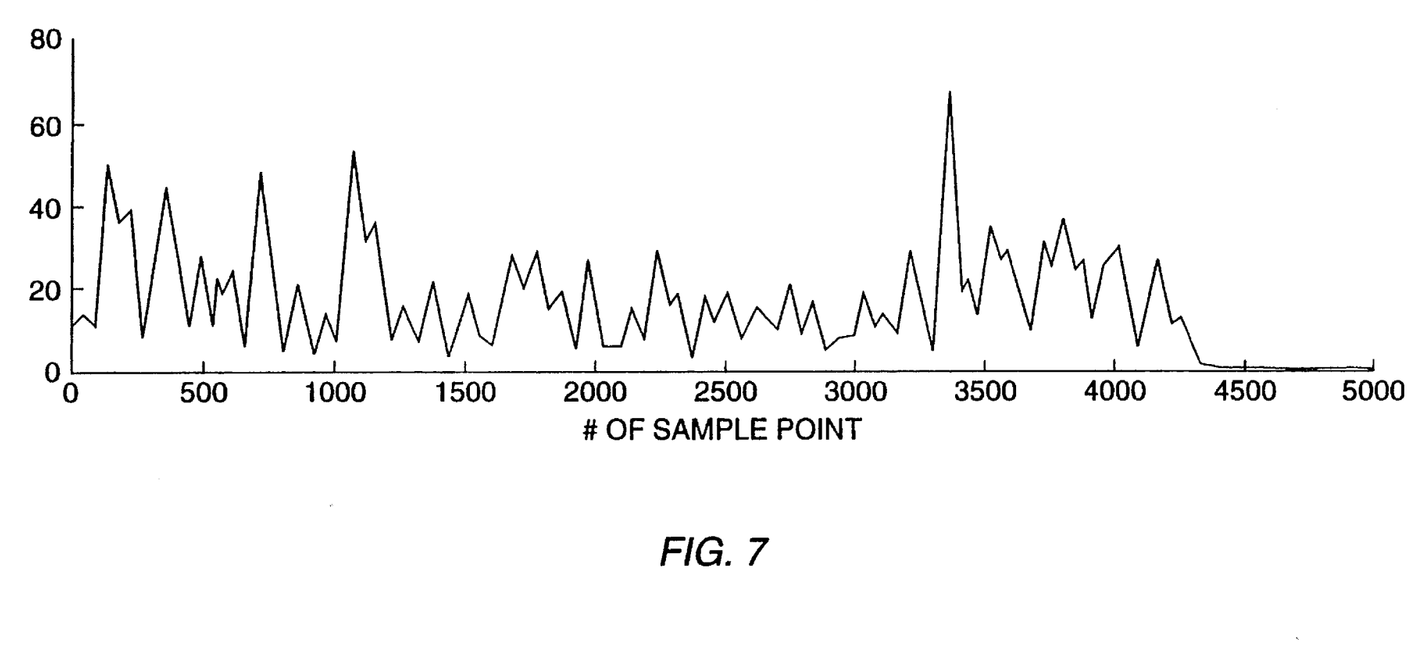
FIG. 7 is a waveform diagram at the conventional envelope detected signal at the output of an amplitude detector corresponding to the waveform diagram of FIG. 6.

FIG. 7 is the waveform at the output of the envelope detector showing an unweighted amplitude signal. This represents the waveform shown in FIG. 6. (In normal imaging modalities envelope amplitude would correspond directly to image pixel brightness.)

Figure 8:
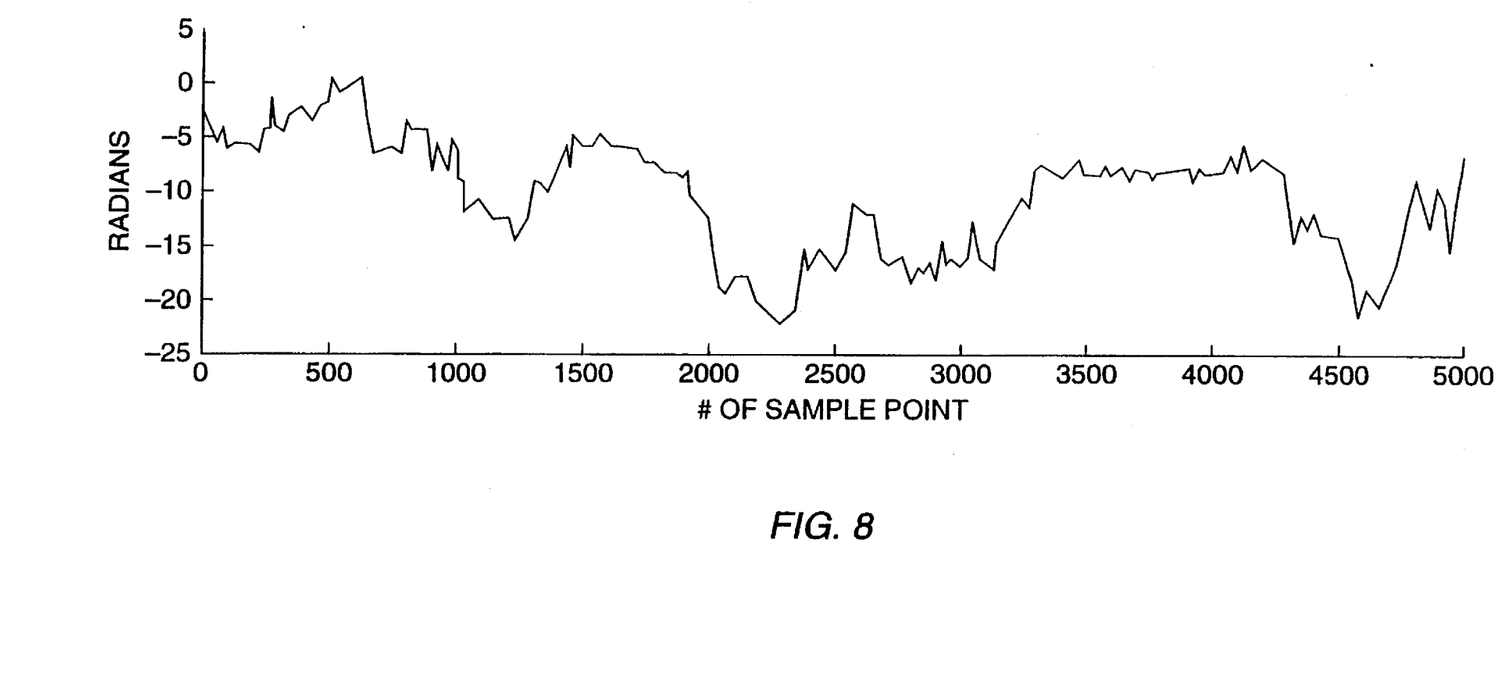
FIG. 8 is a waveform diagram of the cumulative phase difference between two successive vectors of image data, one of which is the waveform diagram of FIG. 6.

FIG. 8 represents the cumulative phase difference between two neighboring vectors of a single frame, one of which is the waveform of FIG. 6. Two vectors at the same position in successive frames of image data would show similar cumulative phase differences. The phase difference is obtained by subtracting the phase angle of the two vectors and unwrapping the phase data; extraction process uses modulo arithmetic. This signal appears at the output of the phase difference data memory 84 (FIG. 3A or 3B).

Figure 9:
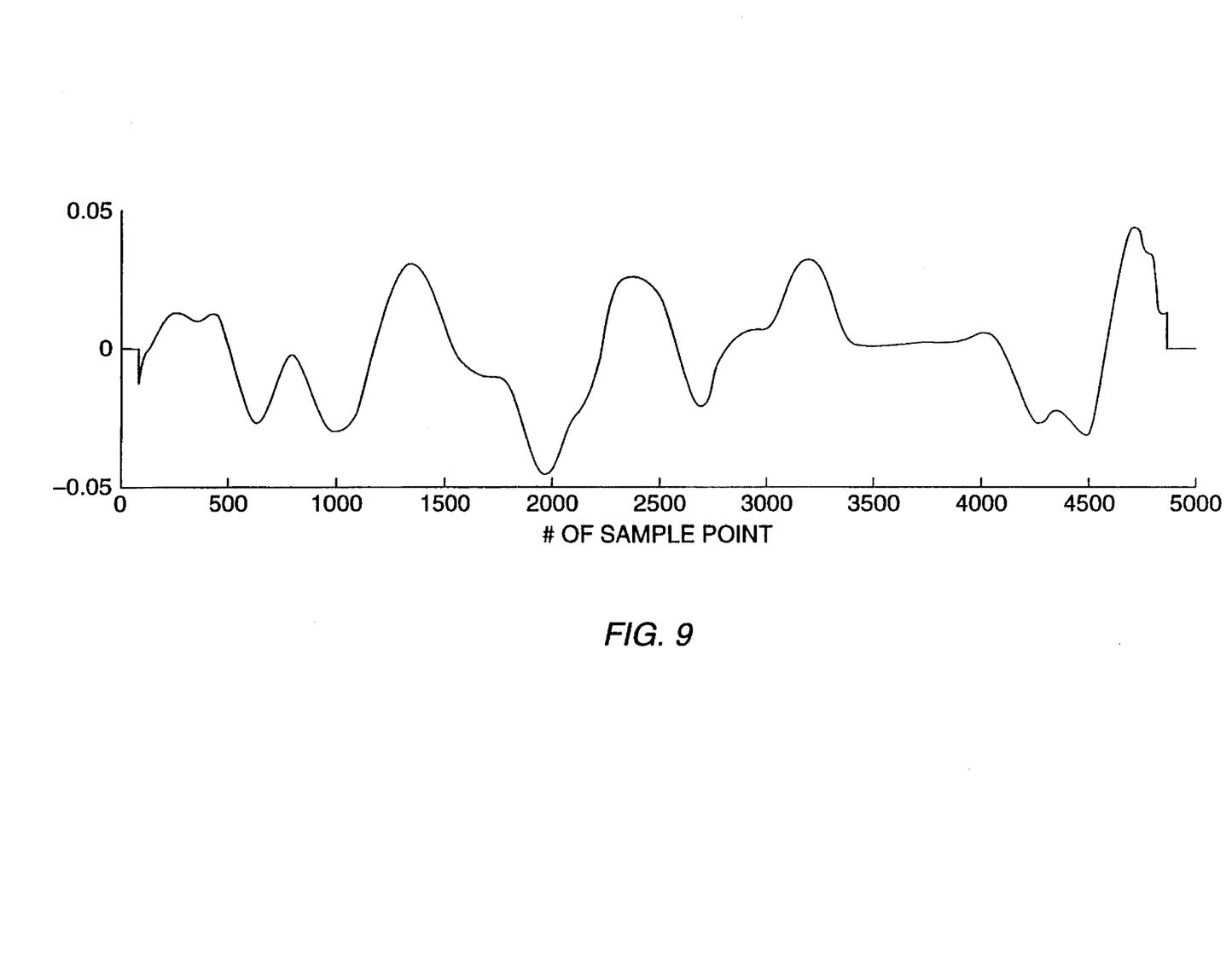
FIG. 9 is a waveform diagram of the slope of the moving average of the phase difference signal in one type of parameter analyzer using data illustrated in the waveform diagram of FIG. 8.

FIG. 9 represents the slope of the moving average of the phase difference signal generated by one type of parameter analyzer using data illustrated in the waveform of FIG. 8. This signal appears at the output of the slope calculator 34 and input to the weighting processor 38 (FIG. 4).

Figure 10:
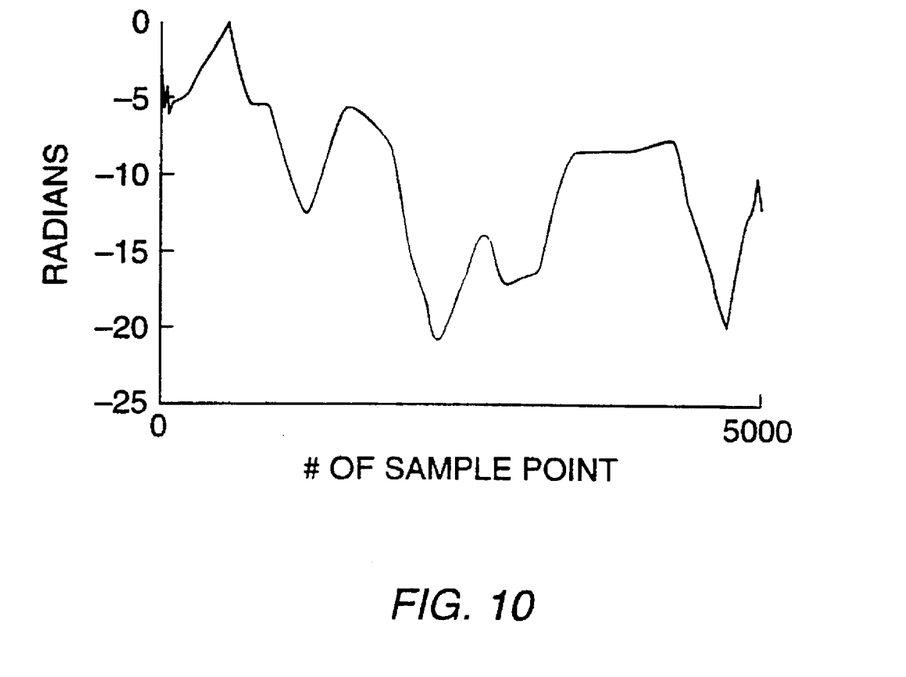
FIG. 10 is a waveform of the moving mean value of the phase difference signal of FIG. 8
Figure 11:
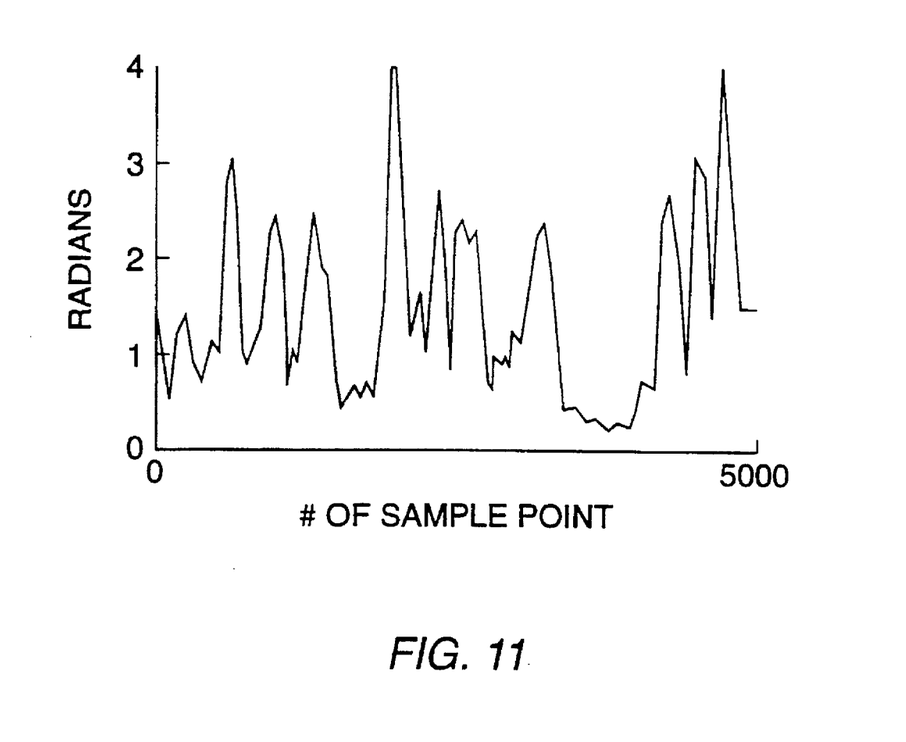
FIG. 11 is a waveform of the moving standard deviation signal in another type of parameter analyzer using data illustrated in the waveform diagram of FIG. 8.

The parameter analyzer 34' generates mean and standard deviation information. FIG. 10 is an exemplary representation of the mean value of the phase difference signal of FIG. 8. Of more direct interest for weighting is the waveform of FIG. 11, which represents the standard deviation using the data illustrated in FIG. 8, as it would appear as input to the weighting processor 38' (FIG. 5).

Figure 12:
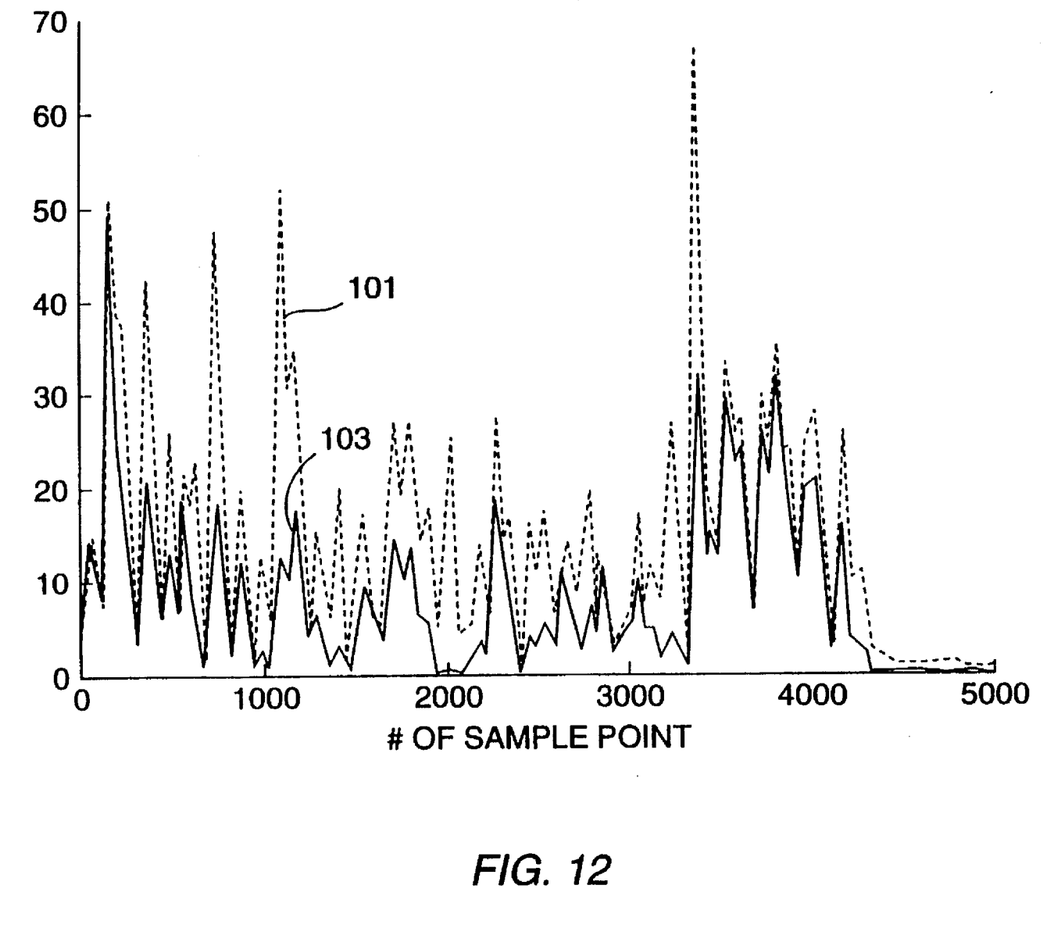
FIG. 12 is a waveform diagram showing the original envelope signal (FIG. 7) overlaid with a slope-weighted envelope signal at the output of a weighting processor.

Two different weighted images can be produced. FIG. 12 shows the waveforms of the original envelope signal 101 (FIG. 7) overlaid with the slope-weighted envelope signal 103 at the output of the weighting processor 38. The slope-weighted signal is the desired image data wherein blood echo signals are suppressed.

Figure 13:
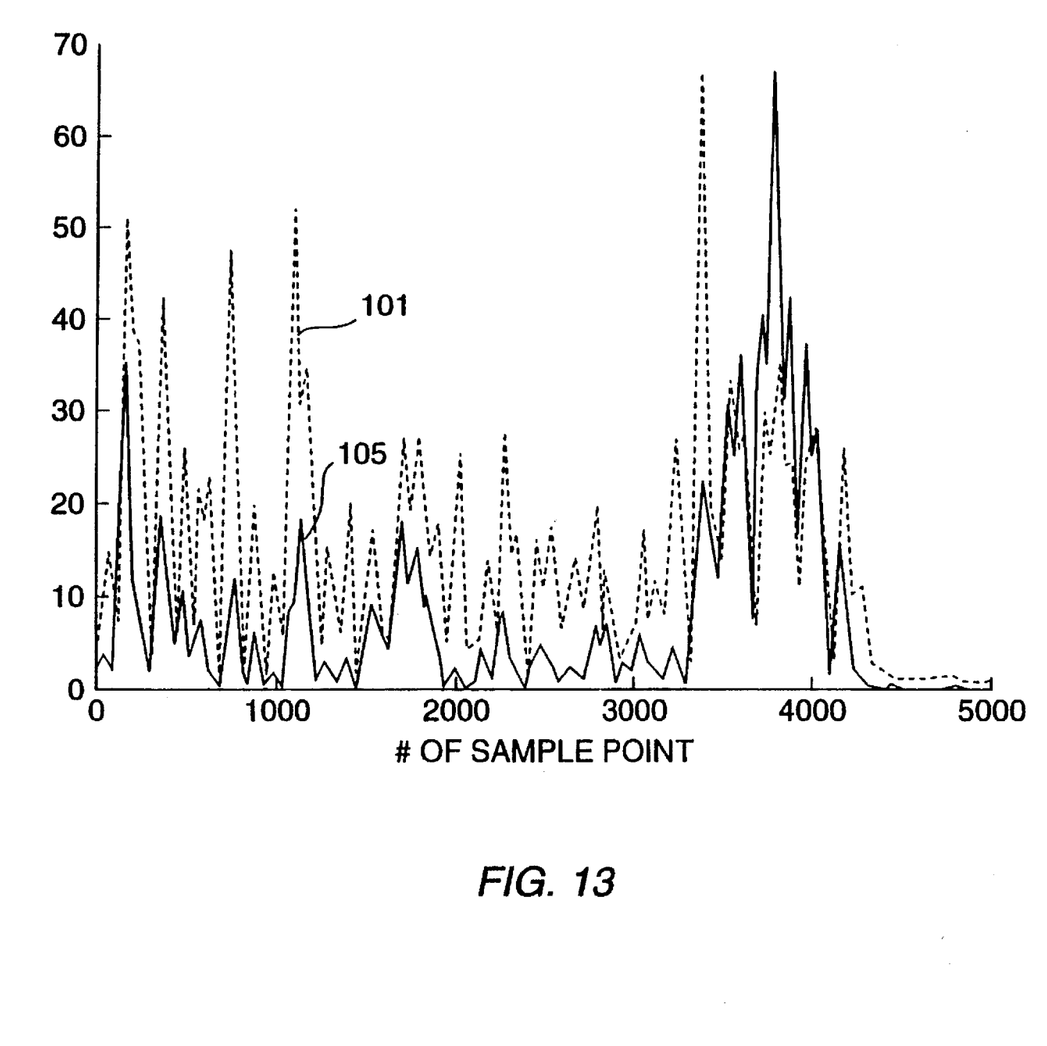
FIG. 13 is a waveform diagram showing the original envelope signal (FIG. 7) overlaid with a standard-deviation-weighted envelope signal at the output of a weighting processor.

FIG. 13 shows the waveforms of the original envelope signal 101 (FIG. 7) overlaid with the standard-deviation-weighted envelope signal 105 at the output of the weighting processor 38'. A waveform having quite different emphasis is produced, although there are evident similarities between waveforms 103 and 105, as both result in suppression of blood echo signals. Specifically, the mean of the processed envelope is reduced in the region corresponding to blood (compared to conventional processing producing waveform 101).

The invention has been particularly shown and described with reference to preferred embodiments. It will be understood by those skilled in the art that the foregoing and other changes in the form and details may be made therein without departing from the spirit or scope of the invention. For example, a still further variation of processing could include removal from the processed image of regions in the image identified as blood, i.e., by including a threshold detection element which compares the conventionally-detected waveform 101 and the weighted waveform 103 or 105 and blanking the image where large differences are evident. It is therefore not intended that this invention be limited, except as indicated by the appended claims.

What is claimed is:

1. A method for enhancing an intravascular ultrasonic blood vessel image comprising the steps of:

directing ultrasonic energy to an intravascular target to produce first ultrasonic echoes from said intravascular target;

converting the first ultrasonic echoes reflected from said intravascular target into a first electrical signal, said first electrical signal including amplitude data and phase data;

separating said first electrical signal into a first component signal and a second component signal;

directing ultrasonic energy to said intravascular target to produce second ultrasonic echoes from said intravascular target;

converting the second ultrasonic echoes reflected from said intravascular target into a second electrical signal;

separating said second electrical signal into a third component signal and a fourth component signal;

obtaining component difference information from said first, said second, said third and said fourth component signals to derive weighting information;

weighting the amplitude data of the first electrical signal with the weighting information to produce processed image data representative of an intravascular image wherein blood images are suppressed; and outputting the processed image data.

2. The method according to claim 1 wherein said component difference information is obtained from said first ultrasonic echoes and said second ultrasonic echoes which are in close spatial proximity.

3. The method according to claim 2 wherein said component difference information comprises phase difference information.

4. The method according to claim 3 wherein said first and third component signals comprise in-phase component signals.

5. The method according to claim 4 wherein said second and fourth component signals comprise quadrature-phase component signals.

6. The method according to claim 5 wherein said weighting information is based on phase difference statistics.

7. The method according to claim 5 wherein said weighting information is based on phase difference slope.

8. The method according to claim 1 wherein said component difference information is obtained from said first ultrasonic echoes and said second ultrasonic echoes which are in close temporal proximity.

9. The method according to claim 8 wherein said component difference information comprises phase difference information.

10. The method according to claim 9 wherein said first and third component signals comprise in-phase component signals.

11. The method according to claim 10 wherein said second and fourth component signals comprise quadrature-phase component signals.

12. The method according to claim 11 wherein said weighting information is based on phase difference statistics.

13. The method according to claim 11 wherein said weighting information is based on phase difference slope.

14. A method for enhancing an intravascular ultrasonic blood vessel image comprising the steps of:

receiving first ultrasonic echoes and second ultrasonic echoes reflected from the direction of ultrasonic energy to an intravascular target, said first and second ultrasonic echoes in close spatial or temporal proximity;

converting the first ultrasonic echoes into a first phase component and a first amplitude component and converting the second ultrasonic echoes into a second phase component and a second amplitude component, said converting step including separating said first phase component into a first in-phase signal and a first quadrature-phase signal and separating said second phase component into a second in-phase signal and a second quadrature-phase signal;

obtaining phase difference information from said first in-phase signal, said second in-phase signal, said first quadrature-phase signal, and said second quadrature-phase signal to derive weighting information;

weighting the first amplitude component with the weighting information to produce processed image data representative of an intravascular image wherein blood images are suppressed; and outputting the processed image data.

15. The method according to claim 14 further comprising converting said first in-phase signal and said first quadrature-phase signal from analog to digital format and converting said second in-phase signal and said second quadrature-phase signal from analog to digital format.

16. The method according to claim 15 further comprising demodulating the first amplitude component using envelope detection prior to said weighting step.

17. The method according to claim 14, wherein said converting step further includes:

converting the first ultrasonic echoes into a first analog electrical signal and converting the first analog electrical signal into a first digital signal, and converting the second ultrasonic echoes into a second analog electrical signal and converting the second analog electrical signal into a second digital signal; and wherein said separating step includes Hilbert transforming the first digital signal to produce said first quadrature-phase signal and Hilbert transforming the second digital signal to produce said second quadrature-phase signal.

18. The method according to claim 17 further comprising:

demodulating the first amplitude component by calculating the square root of the sum of the square of the first in-phase signal and the square of the first quadrature-phase signal prior to said weighting step.

19. The method according to claim 16 or 18 wherein said obtaining step uses phase difference statistics.

20. The method according to claim 16 or 18 wherein said obtaining step uses phase difference slope.

21. A method for enhancing an intravascular ultrasonic blood vessel image comprising the steps of:

obtaining phase difference information from at least two electrical signals representing ultrasonic echoes in close spatial or temporal proximity, the ultrasonic echoes reflected from an intravascular target which has been subjected to ultrasonic energy;

using the phase difference information to generate weighting information;

weighting the amplitude data of one of said at least two electrical signals with the weighting information to produce processed image data representative of an intravascular image wherein blood images are suppressed; and outputting the processed image data.

* * * * *